US006613343B2

(12) United States Patent
Dillingham et al.

(10) Patent No.: US 6,613,343 B2
(45) Date of Patent: Sep. 2, 2003

(54) INJECTABLE INTRAOCULAR ACCOMMODATING LENS

(75) Inventors: Keith Alfred Dillingham, Channel Islands (GB); Hendrik Deuring, Assen (NL); Jöns Gunnar Hilborn, Uppsala (SE); László Garamszegi, Lausanne (CH); Kenneth Albert Hodd, Wales (GB); Hendrik Jan Haitjema, Peize (NL)

(73) Assignee: Pharmacia Groningen BV, Groningen (NL)

( * ) Notice: Subject to any disclaimer, the term of this patent is extended or adjusted under 35 U.S.C. 154(b) by 0 days.

(21) Appl. No.: 09/834,212

(22) Filed: Apr. 12, 2001

(65) Prior Publication Data

US 2002/0071856 A1 Jun. 13, 2002

Related U.S. Application Data

(60) Provisional application No. 60/199,403, filed on Apr. 21, 2000.

(30) Foreign Application Priority Data

Apr. 12, 2000 (SE) ................................................ 0001352

(51) Int. Cl.[7] .................................................. A61F 2/16
(52) U.S. Cl. .................... 424/427; 424/70.12; 623/6.11
(58) Field of Search .............................. 424/427, 70.12; 623/6.11

(56) References Cited

U.S. PATENT DOCUMENTS

| 4,414,694 A | 11/1983 | Choyce |
| 4,573,998 A | 3/1986 | Mazzocco |
| 4,585,456 A | 4/1986 | Blackmore |
| 4,769,035 A | 9/1988 | Kelman |
| 5,116,369 A | * 5/1992 | Kushibiki et al. .............. 623/6 |
| 5,258,025 A | 11/1993 | Fedorov et al. |
| 5,391,590 A | 2/1995 | Gerace et al. |
| 5,411,553 A | 5/1995 | Gerace et al. |
| 5,480,428 A | 1/1996 | Fedorov et al. |
| 5,652,014 A | 7/1997 | Galin et al. |
| 5,776,192 A | 7/1998 | McDonald |
| 5,913,898 A | 6/1999 | Feingold |

FOREIGN PATENT DOCUMENTS

| WO | WO8902252 | 3/1989 |
| WO | WO9305732 | 4/1993 |
| WO | WO9507059 | 3/1995 |
| WO | WO9817205 | 4/1998 |
| WO | WO0022459 | 4/2000 |

OTHER PUBLICATIONS

Quan, *Polymer Engineering and Science*, 29(20):1419–1425 (1989).

* cited by examiner

*Primary Examiner*—Carlos A. Azpuru
(74) *Attorney, Agent, or Firm*—Dinsmore & Shohl LLP

(57) ABSTRACT

The present invention relates to compositions comprising polysiloxanes suitable for the preparation of accommodating intraocular lenses, having a specific gravity of greater than about 1.0, a refractive index suitable for restoring the refractive power of the natural crystalline lens and a viscosity suitable for injection through a standard cannula. The present invention includes intraocular lenses made from said polysiloxane compositions having a Young's modulus less than about 10 kPa.

40 Claims, No Drawings

INJECTABLE INTRAOCULAR ACCOMMODATING LENS

This application claims benefit of U.S. application Ser. No. 60/199,403, filed Apr. 21, 2000,

FIELD OF INVENTION

The present invention relates to an accommodating intraocular lens and to an injectable composition of polysiloxanes having suitable characteristics form an accommodating lens.

BACKGROUND OF THE INVENTION

The human eye is a highly evolved and complex sensory organ. It is composed of a cornea, or clear outer tissue which refracts light rays enroute to the pupil, an iris which controls the size of the pupil thus regulating the amount of light entering the eye, and a lens which focuses the incoming light through the vitreous fluid to the retina. The retina converts the; incoming light into electrical energy that is transmitted through the brain stem to the occipital cortex resulting in a visual image. In the perfect eye the light path from the cornea, through the lens and vitreous fluid to the retina is unobstructed. Any obstruction or loss in clarity within these structures causes scattering or absorption of light rays resulting in diminished visual acuity. For example, the cornea can become damaged resulting in oedema, scarring or abrasions, the lens is susceptible to oxidative damage, trauma and infection, and the vitreous can become cloudy due to hemorrhage or inflammation.

As the body ages, the effects of oxidative damage caused by environmental exposure and endogenous free radical production accumulate resulting in a loss of lens flexibility and denatured proteins that slowly coagulate reducing lens transparency. The natural flexibility of the lens is essential for focusing light onto the retina by a process referred to as accommodation. Accommodation allows the eye to automatically adjust the field of vision for objects at different distances. A common condition known as presbyopia results when the cumulative effects of oxidative damage diminish this flexibility reducing near vision acuity. Presbyopia usually begins to occur in adults during their mid-forties; mild forms are treated with glasses or contact lenses.

Lenticular cataract is a lens disorder resulting from the further development of coagulated protein and calcification. There are four common types of cataracts: senile cataracts associated with aging and oxidative stress, traumatic cataracts which develop after a foreign body enters the lens capsule or following intense exposure to ionizing radiation or infrared rays, complicated cataracts which are secondary to diseases such as diabetes mellitus or eye disorders such as detached retinas, glaucoma and retinitis pigmentosa, and toxic cataracts resulting from medicinal or chemical toxicity. Regardless of the cause, the disease results in impaired vision and may lead to blindness.

Treatment of severe lens disease requires the surgical removal of the lens involving phakoemulsification followed by irrigation and aspiration. However, without a lens the eye is unable to focus the incoming light on the retina. Consequently, an artificial lens is used to restore vision. Three types of prosthetic lenses are available: cataract glasses, external contact lenses and IOLs. Cataract glasses have thick lenses, are uncomfortably heavy and cause vision artifacts such as central image magnification and side vision distortion. Contact lenses resolve many of the problems associated with glasses, but require frequent cleaning, are difficult to handle (especially for elderly patients with symptoms of arthritis), and are not suited for persons who have restricted tear production. Intraocular lenses are used in the majority of cases to overcome the aforementioned difficulties associated with cataract glasses and contact lenses.

IOLs mentioned in the prior art literature usually belong to one of the following categories: non-deformable, foldable, expansible hydrogels and injectable. The earliest IOLs coming into surgical practice are non-deformable implants having rigid structures composed of acrylates and methacrylates. This type of lenses requires a large surgical incision in the capsular bag and is not accommodative. The large incision results in protracted recovery times and the likelihood of introducing astigmatism. In an effort to reduce recovery time and patient discomfort numerous small incision techniques and lenses have been developed.

Present IOLs designed for small incision implantation have elastomeric characteristics and can be made of silicone materials. This type of lenses can be rolled or folded, inserted into the capsular sac then unfolded once inside. Occasionally, the folding of the lens before insertion results in permanent deformation adversely effecting the implant's optical qualities. Foldable lenses meet the requirement of reducing the large surgical incision non-deformable lenses required, but are not accommodative. Moreover, both non-deformable and foldable IOLs are susceptible to mechanical dislocation resulting in damage to the corneal endothelium.

It has further been suggested to use an elastomeric polymer that becomes pliable when heated to body temperature or slightly above in small incision IOL implantation. Once pliable, such a lens would be deformed along at least one axis reducing its size sufficient for easy insertion through a small incision. The lens is then cooled to retain the modified shape until reheated. The cooled lens is inserted into the capsular sac and the natural body temperature warms the lens and it returns to its original shape. The primary drawback to the thermoplastic lens is the limited number of polymers that meet the exacting needs of this approach. Most polymers are composed of polymethylacrylate which have solid-liquid transition temperatures above 100° C. To reduce these transition temperatures modifications of the polymer substrate with the use of plasticizers is required which eventually may leach into the eye.

Dehydrated hydrogels have also been suggested for small incisions techniques. Hydrogel lenses are dehydrated before insertion and naturally rehydrated once inside the capsular sac. However, once fully rehydrated the polymer structure is notoriously weak due to the large amount of water absorbed. The typical dehydrated hydrogel's diameter will expand from 3 mm to 6 mm resulting in a lens that contains about 85% water. At this water concentration the refractive index drops to approximately 1.36 which is unacceptable for an IOL. To achieve a refractive index equal or greater than that of the natural lens (>1.40) a significantly thicker lens is required; this is even further exacerbated when lens diameters exceed 6 mm.

To further develop IOLs and reduce surgical incisions to below 1.5 mm, techniques with injectable IOLs have been suggested, wherein the low viscosity lens material is directly injected into the empty capsular bag and cured in situ as a part of the surgical procedure. In this process the capsular bag is to be used as a mold to form the shape of the lens and thereby contribute control its refraction. There have been several attempts to develop materials suitable for use as injectable IOLs. For example, Gerace et al. describe a fast curing mixture of vinyl-containing polyorganosiloxanes, organosilicone comprising hydride groups and a platinum group metal catalyst used to form an IOL in their U.S. Pat. Nos. 5,278,258, 5,391,590 and 5,411,553 patents. The resulting polymers demonstrate a reduced tendency of discoloration compared to other platinum catalyzed silicone polymers. The '590 patent also discloses a substantially non-functional polymer component of the mixture that has a viscosity at least 50 times greater than the functional polymers. The non-functional component is mixed with the functional components to adjust viscosity to a predetermined specification. Apart from problems with obtaining control over the crosslinking process and finding clinically acceptable conditions, there has been a struggle to perfect the polyorganosiloxane compositions, since they need to have a suitable viscosity for injection, a suitably high refractive index as well as suitable mechanical characteristics after crosslinking, i.e. a suitable modulus. Polydimethylsiloxane (PDMS) has been employed as a material in foldable IOLs and has refractive index similar to that of the natural crystalline lens. This material is also exemplified as a part of the injection mixture in the above-mentioned patents to Gerace et al. PDMS has also been found to have a relatively low viscosity and thereby a tendency to leak out of the desired injection site (i.e. the capsular bag). This is considered in the mentioned U.S. Pat. No. 5,391,590, wherein an additional high viscosity polysiloxane is added to the injection mixture. However, high viscosity silicones have the drawback in that they can entrap air bubbles, which can impair the optical quality of the resulting product. In addition, it has been found that polyorganosiloxanes having a high fraction of dimethylsiloxane units may have an unacceptable low specific gravity with the undesired result that the injected lens material will float on an aqueous layer in the capsular bag. In such a case, it will be difficult to fill the capsular sac completely and requires the surgeon to manually express water in order to maintain the correct lens shape during the curing process. The International Patent Application PCT/EP99/07780 discloses improved polysiloxane terpolymers which have improved characteristics in terms of refractive index, density and viscosity, when compared to the earlier mentioned polysiloxanes. A functionalized form of this type of polysiloxanes is well suited to be part of a thermocurable injectable composition together with a crosslinker and a catalyst. Functional polysiloxanes in this context means that it is provided with functional groups for crosslinking. In a thermocurable system, this typically means that vinyl end groups ("vinyl capping") are introduced on the polymer chain, which can form a crosslinked network with hydride groups on the crosslinker in the presence of the catalyst at given temperature. The International Patent Application PCT/EP99/07781 discloses similar polysiloxane terpolymers which are functionalized with acrylic groups to be suitable for an injectable photocurable composition together with a photoinitiator.

The mentioned polysiloxane terpolymers are capable of solving a number of technical problems related to the preparation of intraocular lenses in-situ in the capsular bag with an injectable composition of functionalized polysiloxanes. However, there is still a need for an injectable polysiloxane material which could form an intraocular lens with sufficiently low elasticity modulus so the lens can undergo accommodation by the forces of the eye. In practical terms this would mean that a lens formed by the polysiloxane material should have a Young's modulus less than 10 kPa and preferably less than about 5 kPa. The purpose of the present invention is to provide improved injectable polysiloxane compositions which admit control of the elasticity modulus of a resulting product, i.e. an intraocular lens implanted with an injection method.

OBJECTS AND SUMMARY OF THE INVENTION

The objects of the present invention are to provide an injectable composition capable of preparing an accommodating intraocular lens directly in the capsular bag of the eye from which an impaired natured lens has been surgically removed. An accommodating lens is defined as lens having a sufficiently low elasticity so it can undergo accommodation under the influence of the eye muscles normally used for the natural lens. This means that the implanted lens resulting from the inventive injectable composition must have a Young's modulus approaching the low value of about 1 kPa of the natural lens. Preferably the inventive compositions can provide lens with as low values as below 10 kPa or even below about 5 kPa which are regarded as clinical conceivable values to restore the accommodation of the patient. It is also an object of the present invention to provide injectable compositions that will form an accommodating lens with a stabilized Young's modulus. This means that the lens has a sufficiently constant Young's implant intraocular lens formed from the injected material.

In its most general form the present invention relates to a composition of polysiloxanes in an injectable ophthalmically acceptable form having a specific gravity of greater than about 1.0, a refractive index suitable for restoring the refractive power of the natural crystalline lens and a viscosity suitable for injection through a standard cannula.

The polysiloxanes of the composition have an refractive index ranges between 1.382 and up to about 1.60, preferably between from about 1.38 to 1.46 and more preferably index ranges from about 1.38 to 1.43, in order to be suitable as a material for the production of intraocular lenses. Most preferably, the inventive polysiloxanes have a specific gravity within the range of about 1.03 to about 1.20. The polysiloxanes should also have a suitable viscosity to be readily injectable through conventional cannula having an 18 Gauge needle dimension or finer dimensions. Preferably, the polysiloxanes should be able to pass through a 21 Gauge needle and more preferably through 25 Gauge needle. To meet with the requirement of being injectable, polysiloxanes according to the present invention have a viscosity less than about 60 000 cSt or preferably less than 5000 cSt. More preferably, the viscosity should be less than about 1500 cSt, wherein the mentioned viscosity values are given at room temperature. The skilled person will be able to relate these requirements to suitable degrees of polymerization.

The polysiloxanes typically consist essentially of different siloxane monomer units having the general formula $—R_aR_bSiO—$, wherein $R_a$ and $R_b$ are the same or different substituted or unsubstituted alkyl or aryl groups bound to the silicone atom. In accordance with the present invention, at least one of the siloxane monomers included in the polysiloxanes has specific gravity greater than about 1.0. According to one aspect of the invention the polysiloxanes has at least one monomer, wherein $R_a$ and $R_b$ are the same or different alkyl or aryl groups of which at least one of said groups is substituted with one or several fluorine atoms. Preferably, the polysiloxanes comprises monomer units, wherein $R_a$ is fluoroalkyl and $R_b$ is alkyl and most preferably the polysiloxanes comprise 3,3,3-trifluoropropylmethylsiloxane monomers. In order to provide the polysiloxanes with the typically high specific gravity, it is preferred that the amount of fluoroalkyl containing monomers exceed about 4 mol %. Further, it is also preferable that one of the siloxane monomers is an arylsiloxane and especially preferred arylsiloxanes are diphenylsiloxane and phenylalkylsiloxane.

In one suitable embodiment, the polysiloxanes of the composition essentially are terpolymers derived from three different siloxane monomers of the general formula $(R_1R_2SiO)_l$ $(R_3R_4SiO)_m(R_5R_6SiO)$, wherein one of the three monomers has a specific gravity greater than about 1.0 and said terpolymer has a refractive index of about 1.41. In order to accomplish polysiloxanes with the mentioned requirements which the inventors have found to be advantageous for obtaining a material suitable for being injected into the capsular bag of the eye, it has been found suitable that $R_1$ and $R_2$ are the same or different lower substituted or unsubstituted alkyl and most preferable both are methyl. $R_3$ and $R_4$ shall be selected among the same or different substituted or unsubstituted aryl and alkyl groups, preferably $R_3$ is phenyl and $R_4$ is phenyl or methyl. $R_5$ and $R_6$ shall be selected among fluoroalkyl and alkyl groups and preferably $R_5$ is trifluoropropyl and $R_6$ is methyl. Alternatively, the inventive polysiloxanes can be higher polymers than terpolymers including but not limited to tetracopolymers with the same monomer types as mentioned.

According to one especially suitable embodiment the, polysiloxanes of the composition essentially are terpolymers having the formula:

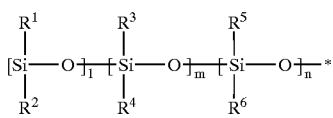

wherein $R^1$ and $R^2$ are independently $C_1$–$C_6$ alkyl; $R^3$ is phenyl; $R^4$ is phenyl or $C_1$–$C_6$ alkyl; $R^5$ is $CF_3(CH_2)_x$ wherein x is 1–5; $R^6$ is $C_1$–$C_6$ alkyl or fluoroalkyl; 1 is in the molar fraction range of 0 to 0.95; m is in the molar fraction range of 0 to 0.7; and n is in the molar fraction range of 0 to 0.65. It is preferred that $R^1$ is methyl, that $R^2$ is methyl, $R^4$ is phenyl, that x is 2, either independently, or in combination. Preferably according to these alternatives $R^6$ is methyl. According to one embodiment, the polysiloxane is a copolymer of diphenyl or phenylalkyl siloxane and dialkyl siloxane. According to further embodiments, the polysiloxane is a copolymer of diphenyl or phenylalkyl siloxane and trifluoroalkyl(alkyl)siloxane, or a terpolymer or higher order polymer of diphenyl and/or phenylalkyl siloxane, dialkyl siloxane and trifluoroalkyl alkyl siloxane. According to a specific preferred embodiment, the polysiloxane is a terpolymer of dimethyl siloxane, diphenyl siloxane or phenylmethyl siloxane and 3,3,3-trifluoropropylmethyl siloxane. Preferably, said polysiloxanes comprise at least about 4 mol % of trifluoropropylmethyl siloxane and 1 to 50 mol % of diphenylsiloxane and/or phenylmethylsiloxane. More preferably said polysiloxanes comprise about 4 to 65 mol % 3,3,3 trifluoropropylmethyl siloxane, 1 to 50 mol % of diphenylsiloxane and dimethylsiloxane monomer units. One suitable polysiloxane composition for being a part of a composition for injection into the capsular bag of the human eye for the formation of IOL comprises about 28 mol % trifluoropropylmethyl siloxane, about 4 mol % diphenyl siloxane and dimethyl siloxane monomer units.

In accordance with the present invention it has been found that a suitable Young's modulus is obtainable with the inventive polysiloxane compositions after a crosslinking process with functional forms of the polysiloxanes and a multifunctional hydride crosslinking agent, if appropriate considerations are taken to the relative of amounts functional polysiloxanes and multifunctional hydride crosslinking agent. The functional polysiloxanes preferably are functionalized to contain vinyl groups capable of participating in a crosslinking reaction with hydride groups of the crosslinking agent. Functional groups for crosslinking will in the context of the present invention in a general sense include unsaturated groups suitable for reaction with silicone bonded hydride (Si—H) groups in the presence of a catalyst, i.e. thermocuring. The skilled person can identify a large number of different alkenyl moieties and different routes of how to synthesize e.g. vinyl functional polysiloxanes. A suitable and commonly employed route is to introduce end-blocking groups of vinyldimethyl siloxane wherein the olefinic vinyl group will enable curing by crosslinking. Alternatively, the functional groups will include acrylic groups capable of participating in a different type of crosslinking reaction induced by a photoinitiator as is disclosed in PCT/EP99/07781, which hereby is incorporated as a reference. The crosslinking agents are of the siloxane or polysiloxane (i.e. a multifunctional organohydrogenpolysiloxane) type carrying at least two, preferably at least three Si—H groups, as disclosed in U.S. Pat. Nos. 5,278,258 and 5,444,106 which documents are incorporated as general references for the crosslinking process. Other suitable crosslinkers are the branched siloxanes mentioned in U.S. Pat. No. 2,877,255. The catalysts can be found among platinum group metal containing catalysts commonly employed for catalyzing the formation of bonds between Si—H groups and vinyl groups as referred to in U.S. Pat. No. 5,278,258. A first suitable crosslinking agent is selected among tetrafunctional crosslinking agents, i.e. those having four hydride groups. An example of a particularly suitable crosslinking agent for the present invention is tetrakis(dimethylsiloxy)silane. A second type of suitable crosslinking agents are difunctional crosslinking agents, i.e. those having two hydride groups. It is to be understood that compositions including crosslinkers with different numbers of functionality (i.e. different amounts of hydride groups per molecule) can be included in the inventive compositions to control the Young's modulus of the final product.

According to a preferred embodiment the crosslinking agent comprises a tetrafunctional crosslinker.

In a first example of this embodiment the polysiloxanes are in a comparatively excessive amount to the crosslinking agent, such that the total amount of functional groups for crosslinking of the polysiloxanes exceeds the number of functional groups participating for the crosslinking process of the crosslinking agent. Suitably this means that the number of vinyl groups of polysiloxanes exceeds the number of hydride groups (Si—H bonds) available on the crosslinkers. After conducting the crosslinking reaction, a fraction of functional polysiloxanes will be unreacted and not be a part of crosslinked network. These polysiloxanes will be able to act as a plasticiser, which modulates the elasticity modulus of a final intraocular lens product.

In a second example of this embodiment, the crosslinking agent is in excess so that an excess of hydride to vinyl bonds is provided. According to this aspect, a fraction of the crosslinking agent rather acts as a chain extender and thereby contribute to a looser more lightly crosslinked network.

In order to safely maintain a stabilized Young's modulus, it has been found necessary to avoid postcuring. Postcuring is a slow process that occurs after the initial fast gellation process has finished and is especially pronounced when an excess of hydride to vinyl groups are used in the crosslinking process, see X Quan in Polymer Engineering and Sci., 1988, 29(20), 1419–1425. In order to overcome postcuring it is therefor preferred to have an excess of vinyl groups over hydride groups in the injectable composition.

In accordance with both these examples, the Young's modulus of the resulting crosslinked product can be reduced in a controlled manner by adding an amount of non-functional polysiloxanes free from functional groups for crosslinking to the compositions. Non-functional groups are defined herein as groups incapable of participating in a crosslinking reaction. Typically a non-functional polysiloxane in accordance with present invention may have end groups of trimethylsiloxane. Advantageously, the functional and non-functional polysiloxanes are compatible to each other in terms of structure, so they are sufficiently miscible in a mixture. Structural differences of the polysiloxanes of the inventive composition may scatter light and appear hazy, misty or opaque rendering them unsuitable for optical applications. Preferably, the functional and non-functional polysiloxanes essentially are the same polysiloxane of the groups being defined above, i.e. most preferably essentially the same terpolymer. A composition of functional and non-functional polysiloxanes will further comprise a crosslinking agent capable of reacting with the functional groups of the polysiloxanes an effective amount of a catalyst so as to cure the composition at a suitable temperature into a final product. The resulting crosslinked composition will have a network formed by the functional polysiloxanes and the crosslinking agent within which the non-functional polysiloxanes are distributed and will act as a plasticizer for the product. The non-functional polysiloxanes have the effect of swelling the network and increasing the space between the crosslinks. Considering the risk of diffusion of the non-functional polysiloxanes from an in-situ cured intraocular lens through the capsular bag into surrounding eye, these polymers are preferably selected with sufficiently high a molecular weight so as to substantially prevent from any such diffusion. Since there is a relation between molecular weight, polysiloxane viscosity and injectability of the composition, considerations must be taken to that an increase in the non-functional polysiloxane molecular weight does not compromise the overall viscosity of the composition in a way so it no longer readily can be injected with a standard cannula as outlined above: In one aspect of this embodiment, the viscosity of the non-functional polysiloxanes does not exceed the viscosity of the polysiloxanes having functional groups for crosslinking. In accordance with this aspect, one fraction of the polysiloxanes manufactured to be included in the composition can be provided with functional vinyl groups (e.g. vinyl end-capped), while the other fraction is included in its non-functionalized form. By conducting tests in vitro human capsular bag tissue, it has been found that the non-functional polysiloxanes preferably shall have molecular weight exceeding a value of about $M_n=5000$ g/mol to substantially reduce the risk of diffusion of such polysiloxanes from the capsular bag. Preferably, the molecular weight shall exceed $M_n=7000$ g/mol and even more preferably exceeding about 10000 g/mol.

In accordance with a specific example of the invention, the composition comprises non-functional polysiloxanes in excess to functional polysiloxanes. In this example the functional groups are vinyl groups and the relative amount of functional polysiloxanes to crosslinking agent in the composition is selected such that a relationship between hydride groups to vinyl groups is provided is 0.8:1, or with larger excess of vinyl groups. Suitably, the polysiloxanes are terpolymers of the structures defined according to above. Typical values for when using a tetrafunctional crosslinking agent are 50% to 93% (wt) non-functional polysiloxane and values within a similar range. For this type of compositions, the resulting elasticity modulus can be controlled by modifying the quantitative relationship between functional and non-functional polysiloxane and between the functional polysiloxane and the crosslinker.

One composition found to provide a suitable Young's modulus below 5 kPa shortly after crosslinking includes a polysiloxane constituent of about 20% poly(dimethyl-co-diphenyl-co-trifluoropropylmethyl)siloxane terpolymer functionalized with vinyl groups (i.e. end-capped) and about 80% non-functional terpolymer of the same structure, tetrakis(dimethylsiloxy)silane as crosslinker in an amount such that a relationship of hydride to vinyl bonds of about 1.8:1 is obtained and a platinum metal catalyst.

Another composition found to provide a suitably stable Young's modulus below about 5 kPa without postcure includes a polysiloxane constituent of about 20% poly (dimethyl-co-diphenyl-co-trifluoropropylmethyl)siloxane terpolymer functionalized with vinyl groups (i.e. end-capped) and about 80% non-functional terpolymer of the same structure, tetrakis(dimethylsiloxy)silane as crosslinker in an amount such that a relationship of hydride to vinyl bonds of about 0.8:1 is obtained and a platinum metal catalyst.

An alternative manner of obtaining a controlled reduction of the Young'modulus according to the present invention is to further comprise a difunctional crosslinker (i.e. a difunctional hydride) to the tetrafunctional crosslinker. An addition of difunctional (hydride) crosslinker is applicable on the composition discussed above. For example, a composition comprising functional polysiloxane and tetrafunctional crosslinker in amounts such that functional vinyl to hydride bonds has molar relationship of 1:1 or close to 1 (the number vinyl and hydride matches each other) will provide a substantially complete crosslinking reaction, since substantially every polysiloxane and crosslinker molecule will be attached to the network. In such a composition the obtainable Young's modulus will be at its maximum, or close thereto. For this type of composition, a controlled reduction of the Young's modulus is obtained by adding a fraction of difunctional crosslinker to the composition of tetrafunctional crosslinker. The difunctional crosslinker preferably is a short chain polydimethylsiloxane chain with hydride groups in its ends, which will act as a chain extender during the crosslinking. The addition of a difunctional crosslinker is a suitable alternative or complement to adding non-functional polysiloxanes as a means to obtain a controlled Young's modulus reduction of crosslinked articles prepared with the inventive compositions, since it reduces the risk of free extractable polysiloxanes not being a part of network.

Within the general concept of the present invention it is possible to modify and control the Young's modulus by changing the amount vinyl to hydride groups (i.e. the relative amount of functional polysiloxane to multifunctional hydride crosslinking agent), the concentration of non-functional polysiloxane and adding a chain extender (i.e. a difunctional hydride crosslinking agent. Post curing effect can be prevented by a skilled person by selecting appropriate compositions according to the invention and thereby ensuring stable material properties. The skilled person will readily identify combinations of these alternatives and when it is applicable.

According to an alternative embodiment of the invention, the polysiloxane composition may comprise only non-functional polysiloxanes. The non-functional polysiloxanes are selected among the same polysiloxanes as defined above with a preference for the terpolymers.

It is to be understood by the skilled person that the compositions are prepared by mixing a formulation of polysiloxanes and catalyst with a formulation of the crosslinking agent, just prior to its use. It is also to be understood that compositions can comprise further conventional constituents, such as agents for affecting the crosslinking and agents commonly associated with the production of IOLs from silicone materials, e.g. UV light absorbers.

Examples of preferred routes to produce the polysiloxanes of the inventive compositions and how to produce intraocular lenses from these compositions are given below.

DETAILED DESCRIPTION OF EXEMPLARY EMBODIMENTS

The types of siloxane monomers useful in preparing the IOLs of this preferred embodiment include, but are not limited to, methyl and substituted methyl siloxanes, phenyl siloxanes and trifluoropropyl methyl siloxanes with individual specific gravities ranging between 0.97 and 1.28. The high specific gravity silicone copolymers of the present invention are prepared by mixing a plurality of these compounds in a predetermined ratio to achieve a desired specific gravity and refractive index.

According to one embodiment, three siloxane monomers are mixed together with a suitable end blocker and dried in a reduced atmosphere under controlled thermal conditions. The reaction mixture is then catalyzed to induce copolymerization in an inert atmosphere. The reaction is allowed to continue for a predetermined time in a precise thermal environment then terminated. Next, the reaction product is washed, precipitated and dried. The specific gravity, refractive index and mean molecular weight are determined.

In another embodiment of the present invention three siloxane monomers are mixed together with a suitable end blocker and dried in a reduced atmosphere under controlled thermal conditions as before. The reaction mixture is then catalyzed to induce copolymerization in an inert atmosphere. The reaction is allowed to continue for a predetermined time in a precise thermal environment then terminated. Next, the reaction product is washed, precipitated and dried. The resulting precipitate is then re-dissolved in a suitable solvent and filtered to enhance clarity. The specific gravity, refractive index and mean molecular weight are determined. Changes in the reactants, their relative concentrations and reaction conditions will result in a variety of end products with different specific gravities and refractive indices. The benefits of these differences will become apparent to one skilled in the art from the specific examples below.

According to the methods of the present invention, the ratio of siloxane monomer reactants necessary to achieve a desired refractive index and specific gravity can be approximated mathematically. If N is the desired IOL's refractive index and P is the specific gravity of the lens' copolymer and where $n_{1-3}$ are the refractive indices and $p_{1-3}$ are the specific gravities of the monomer reactants then the following mathematical relationship can be used:

$$N = x_1 n_1 + x_2 n_2 + x_3 n_3$$

$$P = x_1 p_1 + x_2 p_2 + x_3 p_3$$

Where $x_{1-3}$ represent the ratio of the individual siloxane monomer reactants required to achieve an IOL with the desired optical and physical properties and $x_1 + x_2 + x_3 = 1$.

Having an injectable silicone lens with a specific gravity greater than 1.0 will greatly simplify the injection process and represents a significant improvement over previously suggested materials for injectable lens materials. Prosthetic lenses made by the process described herein are compliant and retain the refractive index of the natural lens making them ideal as corrective lenses as well as replacements for damaged and cataractous lenses.

The present invention improves considerably on previously suggested polysiloxane based materials for injectable IOLs due to its increased specific gravity to above 1.0, so displace residual water after its injection into the capsular sac's aqueous environment. This characteristic will reduce post-injection manipulation of the surgeon and will assure that the lens will assume a natural position and configuration. In accordance with the methods of the present invention an injectable IOL material is formed that greatly simplifies the injection, positioning and curing process. By the mentioned selection of siloxane monomers a high density injectable material can be provided with a controlled suitable refractive index comparable to that of the natural lens without compromising the other important requirements including a viscosity suitable for injection. This will greatly contribute to that is possible to adjust the refractive outcome of the injected lens formed with the capsular bag as a mold by having suitable fractions of siloxane units contributing to a high refractive index and siloxane units contributing to a high density. Another advantage of this invention is that extremely compliant nature fully cured lenses can be obtained. If a conventional foldable silicone lens is considered to have a stiffness of 100, a cured injectable lens made from the material of the present invention could be designed to have a stiffness ranging from zero to five. Therefore, lenses made from the material described herein can be accommodative and respond naturally to the changes in the eyes' shape as focal length is adjusted. The accommodative nature of lenses fabricated from materials of the present invention would make them particularly suitable for corrective purposes besides replacements for diseased natural lenses and is considered within the scope of this invention. An unexpected, and beneficial, advantage of the present invention is the optically smooth surface formed after the lens has cured in situ.

The following examples are offered as being illustrative of the principles of the present invention and not by way of limitation.

EXAMPLE 1

Preparation of poly(dimethyl-co-methylphenyl-co-trifluoropropylmethyl)siloxane

To a dry 50 ml flask were added siloxane monomers: hexamethylcyclotrisiloxane, 6.0 g, 3,3,3-trifluoropropylmethylcylclotrisiloxane, 7.3 g, 1,3,5-trimethyl-1,3,5-triphenylcyclotrisiloxane, 1.7 g (1.55 ml), and an end-blocker, 1,3-divinyltetramethyldisiloxane, 0.14 g (0.17 ml). The mixture was dried under vacuum at 80° C. for 30 minutes, then purged with argon. The temperature was raised to 140° C. and potassium silanolate catalyst, 7 mg, was added to initiate polymerization. The reaction proceeded quickly as indicated by an increase in viscosity. After about 30 minutes the mixture clarified. After about 3 hours the temperature was raised to 160° C. and the reaction continued for a further 3 hours, after which the reaction was cooled to room temperature. The polymer was cleaned using a procedure of dilution with tetrahydrofuran and precipitation in methanol, then dried. The dried silicone product was glass clear, with refractive index: 1.4070 (calculated: 1.410), specific gravity: 1.116 (calculated: 1.104), and molecular weight by GPC 25,000. Crosslinking of the polymer produced a clear silicone gel.

EXAMPLE 2

Preparation of poly(dimethyl-co-methylphenyl-co-trifluoropropylmethyl)siloxane

A reaction mixture was prepared according to Example 1 except that the siloxane monomers were hexamethylcyclotrisiloxane, 9.0 g, 3,3,3-trifluoropropylmethylcylclotrisiloxane, 4.65 g, 1,3,5-trimethyl-1,3,5-triphenylcyclotrisiloxane, 1.35 g (1.23 ml). The resulting silicone polymer product was glass clear, the refractive index was 1.4082 (calculated: 1.410), specific gravity was 1.066 (calculated: 1.056) and the molecular weight by GPC was 26,000.

EXAMPLE 3

Preparation of poly(dimethyl-co-diphenyl-co-trifluoropropylmethyl)siloxane

To a dry 50 ml flask were added siloxane monomers:hexamethylcyclotrisiloxane, 7.5 g, 3,3,3-trifluoropropylmethylcyclotrisiloxane, 6.66 g, hexaphenylcyclotrisiloxane, 1.68 g, and an end-blocker, 1,3-divinyltetramethyldisiloxane, 0.28 g (0.34 ml). The mixture was dried under vacuum at 80° C. for 30 minutes, then purged with argon. The temperature was raised to 140° C. and potassium silanolate catalyst, circa 7 mg, was added to initiate polymerization. The reaction proceeded quickly as indicated by an increase in viscosity. After about 30 minutes the solution was almost clear with some residue at the bottom of the reaction vessel. The viscosity of the reaction mixture was decreasing. After about 2 hours the temperature was raised to 160° C. and the reaction continued for a further 3 hours, after which the reaction was cooled to room temperature. The polymer was washed with tetrahydrofuran and precipitated in methanol, then dried. The dried silicone product was slightly hazy. The material was dissolved in tetrahydrofuran, filtered through a 0.45 micrometer filter, and again dried, yielding a glass clear silicone polymer. The refractive index was 1.4095 (calculated:1.424), specific gravity was 1.10 (calculated: 1.094) and the molecular weight by GPC was 18,000. Crosslinking of this material yielded a clear silicone gel.

EXAMPLE 4

Preparation of poly(dimethyl-co-diphenyl-co-trifluoropropylmethyl)siloxane

To a dry 1000 ml flask were weighed in order: octaphenylcyclotetrasiloxane, 90.61 g, 3,3,3-trifluoropropylmethylcylclotrisiloxane, 101.88 g, octamethylcyclotetrasiloxane, 368.27 g, and an $\alpha,\omega$-divinyl dimethylsiloxane oligomer end-blocker (Mn 1287 by NMR analysis), 40.93 g. The flask was equipped for reflux and reagents dried under vacuum on a bath at 80° C. for 30 minutes. The system was purged with nitrogen, and potassium silanolate (Mn 395), 267 mg, added. The bath temperature was increased to 160° C. and the mixture heated and stirred for 20 hours, yielding a clear colourless polymer mixture. After cooling, the product was diluted with 420 ml dichloromethane, and washed four times with 420 ml portions of water, the first portion being acidified with 3.0 ml of 0.1N HCl and the second portion with 0.6 m 1.0N HCl (the third and fourth portions were not acidified). The polymer was then washed twice with 420 ml portions methanol, diluted with 180 ml tetrahydrofuran, and washed twice more with methanol, as before. The solvent was then removed under vacuum over a few hours, with heating on a bath at 100° C., to a pressure of below 1 mbar. The polysiloxane product was clear and colourless, with refractive index 1.428 (calculated: 1.432) and density 1.04 (calculated: 1.043). Viscosity at 25° C. was 1802 cP. H-NMR, 500 MHz, gave unit mole ratios:dimethyl/diphenyl/trifluoropropyl/divinyltetramethyl of 0.819/0.071/0.105/0.00494 (monomer ratios were: 0.827/0.070/0.099/0.00483), implying Mn 18,600. GPC gave Mn 18,500 and Mw 36,600.

EXAMPLE 5

Preparation of poly(dimethyl-co-diphenyl-co-trifluoropropylmethyl)siloxane

The polymerization method of Example 3 was repeated on a 125 g reagents scale, employing octaphenylcyclotetrasiloxane, 34.88 g, 3,3,3-trifluoropropylmethylcyclotrisiloxane, 25.25 g, octamethylcyclotetrasiloxane, 56.4 g, and an $\alpha\omega$-divinyl dimethylsiloxane oligomer end-blocker (Mn 1287), 8.50 g, and potassium silanolate, 55 mg. The work-up differed from Example 3, using chloroform, 57 ml, to dilute the polymer, followed by three washes with water and two with methanol, all 88 ml portions, then dilution with 44 ml tetrahydrofuran, followed by two more washes with 88 ml portions methanol, then vacuum stripping to <1 mbar on a bath at 100° C. The clear colourless product had refractive index 1.455 (calculated: 1.460) and density 1.08 (calculated: 1.080). Viscosity at 25° C. was 3324 cP. H-NMR, 500 MHz, gave unit mole ratios: dimethyl/diphenyl/trifluoropropyl/divinyltetramethyl of 0.697/0.158/0.140/0.00570 (monomer ratios were: 0.713/0.146/0.135/0.00549), implying Mn 18,600. GPC gave Mn 16,900 and Mw 33,400.

EXAMPLE 5a

Preparation of non-functional poly(dimethyl-co-diphenyl-co-trifluoropropylmethyl)siloxane To a dry 500 ml flask were weighed in order:octaphenylcyclotetrasiloxane, 38.10 g; 3,3,3-trifluoropropylmethylcyclotrisiloxane, 42.90 g; octamethylcyclotetrasiloxane, 139.82 g; and trimethylsiloxy-ended dimethylsiloxane oligomer, Mn 1200, 30.00 g. The mixture was dried by heating under vacuum at 80 C. for 30 minutes, then purged with nitrogen and potassium silanolate initiator, 0.12 g, added. The polymerization mixture was heated for 20 hours on a bath at 160 C., then allowed to cool. The reaction product was diluted with dichloromethane, 175 ml, and washed with water, 175 ml, to which was added 0.1N HCl in small portions until the washings tested just acidic. The product received three more water washings, then two methanol washes, all 175 ml each, before dilution with THF, 75 ml, and a final methanol wash. The product was then heated on a bath at 100 C. under vacuum to remove volatile components, the vapour pressure falling to 0.4 mbar over 4 hours. Yield was 191.3 g (76.2%) of a clear colourless fluid, Mn 11,980; Mw 21,250 by GPC.

EXAMPLE 6

Curing of Prepolymers

The silicone polymers were prepared for curing by formulating two parts, a Part A containing platinum catalyst in the form of the 1,3-divinyltetramethyldisiloxane complex, and a Part B containing crosslinker and siloxane inhibitor. The preferred crosslinker was tetrakisdimethylsiloxysilane, TKDMSS, but a polymeric silicon hydride (Gelest/ABCR HMS-151, a copolymer of methylhydrosiloxane and dimethylsiloxane having nominal Mn 1900–2000 and 15–18 mol % MeHSiO units) is here also reported for comparison. Optimum ratios of catalyst, crosslinker, and inhibitor were determined by studying the curing profiles of silicone mixtures using a rheometer (Rheometrics RDA II, with determination of the moduli of the cured materials. Mixtures were formulated to give gel times circa 15–75 minutes at 20° C. Tests were performed at 35° C. using 25 mm diameter plates with 1 mm spacing. Frequency and strain sweeps were regularly performed on the materials. Mixtures for testing were prepared by accurately weighing portions of Parts A and B, mixing for 2 minutes, and degassing under reduced pressure before transferring the mixture to the plates. The disks obtained from the mixtures were clear and colourless. The results obtained are illustrated by the following examples:

EXAMPLE 6(a)

Prepolymer prepared in Example 4 was formulated as Part A, containing circa 8 mg/kg platinum, and Part B containing 18.2 mg TKDMSS/g Part B, plus siloxane inhibitor. The mixture was analyzed on the rheometer in different weight ratios of B/A at 35° C., determining shear moduli, G', after 3000 seconds. The results for ratios B/A were:ratio: 0.86, G' 199.2 kPa; ratio: 1.00: G' 217.2 kPa; ratio: 1.15, G' 214.5 kPa.

EXAMPLE 6(b)

Prepolymer prepared as per Example 4 was formulated as Part A, containing circa 12 mg/kg platinum, and Part B containing 8.23% ww polymeric silicon hydride, Gelest/ABCR HMS-151, plus siloxane inhibitor. The mixture was analyzed on the rheometer at 35° C. as above. Shear moduli, G', after 3000 seconds for ratios B/A were:ratio: 0.821, G' 100.7 kPa; ratio: 1.00: G' 167.9 kPa; ratio: 1.22, G' 193.2 kPa; ratio: 1.52, G' 184.0 kPa.

EXAMPLE 6(c)

Composition Comprising 20% Vinyl-ended Polysiloxane and 80% Non-functionalized Polysiloxane Having Stoichiometric Excess of Hydride Crosslinker Here, non-functionalized silicone was employed to yield a cured material having a modulus comparable with the human lens. Prepolymer prepared as per Example 4 but with slightly increased vinyl end-capper, having Mn 16990, was formulated as Part A containing circa 18 mg/kg Pt, and Part B containing 31.6 mg TKDMSS/g Part B. Components were weighed in order: Part A, 0.207 g; non-functionalised silicone of Example 5(b) 1.61 g; and Part B, 0.213 g; and mixed and degassed. Gel time of the mixture was 14 minutes at 21 C., and cured at 35 C. the material had storage modulus, G', 1.17 kPa.

EXAMPLE 6(d)

Composition Comprising 20% Vinyl-ended Polysiloxane and 80% Non-functionalized Polysiloxane Having Various Stoichiometric Excess of Hydride Crosslinker The vinyl-ended silicone prepolymer of Example 6(c), Mn 16990, was formulated into batches of Parts A and B containing differing concentrations of catalyst and crosslinker. A series of curing experiments at 35 C. were then performed in which 0.2 g each of Parts A and B were mixed in 1.0:1.0 ratio with 1.6 g of non-functional polysiloxane fluid of Example 5(b) Mn 11,980. The concentrations of platinum catalyst were adjusted in the range 39–146 mg/kg total mixture as appropriate to give acceptable gel time, as rates of reaction increased with increasing crosslinker concentration. For different concentrations of TKDMSS crosslinker giving different ratios of the functionalities SiH/vinyl (mole/mole) the storage moduli, G', were as follows: ratio 1.01, G' 1.58 kPa; ratio 1.25, G' 7.58 kPa; ratio 1.51, G' 3.47 kPa; ratio 1.78, G' 1.19 kPa. It is noted that highest modulus required stoichiometric excess of crosslinker in the fluid swollen network.

EXAMPLE 6(e)

Vinyl-ended Prepolymer Plus Various Stoichiometric Excesses of Hydride Crosslinker The vinyl-ended silicone prepolymer of Example 6(c), Mn 16990, was formulated into stock batches of Parts A and B; Part A containing ca.22 mg/kg platinum as its 1,3-divinyltetramethyldisiloxane complex, and stock Part B containing 56.4 mg/g of tetrakisdimethylsiloxysilane crosslinker plus 0.74 mg/g of 1,3-divinyltetramethyldisiloxane as inhibitor. Curing formulations were then prepared in which various dilutions of Part B in the base prepolymer (Mn 16990) were made so that the ratio of Part A to 'diluted Part B' was 1.0/1.0 in each case, but the molar ratio hydride/vinyl could be varied. The ratios, SiH/vinyl, and their respective measured storage moduli, G', were: 1.0/1.0, 214.5 kPa; 1.5/1.0, 163.2 kPa; 2.0/1.0, 51.6 kPa; 2.5/1.0, 4.11 kPa; and 3.0/1.0, 0.54 kPa (for this final measurement, the Part A was diluted to 33% in 67% base prepolymer to slow the reaction).

EXAMPLE 6(f)

Composition of Comprising Vinyl-ended Prepolymer Having Various Stoichiometric Defecits of Hydride Crosslinker The vinyl-ended silicone prepolymer of Example 6(c), Mn 16990, was formulated into stock batches of Parts A and B; Part A containing ca.66 mg/kg platinum as its 1,3-divinyltetramethyldisiloxane complex, and stock Part B containing 19.2 mg/g of tetrakisdimethylsiloxysilane crosslinker plus 0.25 mg/g of 1,3-divinyltetramethyldisiloxane as inhibitor. Curing formulations were then prepared in which various dilutions of Part B in the base prepolymer (Mn 16990) were made so that the ratio of Part A to 'diluted Part B' was 1.0/1.0 in each case, but the molar ratio hydride/vinyl could be varied. The ratios, SiH/vinyl, and their respective measured storage moduli, G', were: 1.0/1.54, 34.60 kPa; 1.02.09, 3.19 kPa; 1.0/2.56, 0.25 kPa.

EXAMPLE 6(g)

Compositions Comprising 60% Vinyl-ended Silicone, 40% Non-functionalized Silicone Having Various Stoichiometric Defecits of Hydride Crosslinker The vinyl-ended silicone prepolymer of Example 6 (c), Mn 16990, was formulated as per Example 6 (f) into Parts A containing ca. 66 mg/kg platinum as its 1,3-divinyltetramethyldisiloxane complex, and Part B containing 19.2 mg/g of tetrakisdimethylsiloxysilane crosslinker plus 0.25 mg/g of 1,3-divinyltetramethyldisiloxane as inhibitor. A formulation was prepared from Part A, 0.761 g, non-functional silicone of Example A, 1.007 g, base vinyl-ended prepolymer, 0.383 g, and Part B, 0.389 g, thus giving a composition that was 60.4% vinyl functionalized silicone and 39.6% non-functionalized silicone, with molar hydride/vinyl ratio of 1.0/1.98. The storage modulus, G', of the cured material was 0.93 kPa.

EXAMPLE 6(h)

Compositions Comprising 16% Vinyl-ended Silicone, 84% Non-functionalized Silicone Having Various Stoichiometric Defecits of Hydride Crosslinker and no Postcure The vinyl-ended silicone prepolymer of Example 6(c), Mn 16990, was formulated a Parts A containing ca. 89 mg/kg platinum as its 1,3-divinyltetramethyldisiloxane complex, and Part B containing 0.2680% w/w of tetrakis-dimethylsiloxysilane crosslinker plus 0.043% w/w of 1,3-divinyltetramethyldisiloxane as inhibitor. A formulation was prepared from equal amounts of Part A and Part B, 0.389 g with molar hydride/vinyl ratio of 0.8/1.0. The storage modulus, G', of the cured material was 0.90 kPa. After a 13 weeks follow-up period of the mudulus no change was found and thus no postcure was present.

EXAMPLE 7

Implantation of Silicone Material Into Pig Cadaver Eyes

A fresh pig cadaver eye was prepared, with small aperture incision into the capsular bag and removal of the crystalline lens. The silicone composition was prepared from the pre-polymer of Example 4, having refractive index 1.428, with Part A containing ca. 12 mg/kg platinum as a divinyltetram-ethyldisiloxane complex, and Part B containing tetrakisdim-ethylsiloxysilane crosslinker, 18.9 mg/g mixture, with silox-ane inhibitor. Gel time was circa16 minutes at 20° C. Silicone for injection was prepared by mixing equal weights of Parts A and B in a Teflon pot, taking up in a syringe, vacuum degassing, and then injecting into the capsular bag via a 21 gauge cannula, so as to refill the bag and give appropriate curvature. After curing (ca. 45 minutes from the start of mixing) the lens was removed from the eye. The transparent tack-free lens had anterior radius 10.1±0.4 mm, posterior radius 5±0.1 mm, thickness 5.33±0.03 mm, and diameter 9.2±0.1 mm. Its power in air was 115±2 diopter, and focal length 8.7±0.1 mm (in water, lens power was 29.1±0.5 diopters, and focal length 45.7±0.8 mm). The natural length 8.7±0.1 mm (in water power was 29.1±0.5 diopters, and focal length 45.7±0.8 mm). The natural crys-talline lens of the pig has higher $R^1$ than that of the human lens. From the measured dimensions of 11 pig lenses it was calculated that an $R^1$ of circa 1.51 is required to restore natural refractive power in a refilled pig lens.

EXAMPLE 8

Implantation of Silicone Material Into a Human Cadaver Eye

A human cadaver eye was prepared, with small aperture incision into the capsular bag and removal of the crystalline lens. The silicone composition was prepared and a lens made as per Example 7. The transparent tack-free lens had anterior radius 8.7±0.5 mm, posterior radius 6.2±0.1 mm, thickness 4.11±0.06 mm, and diameter 8.2±0.1 mm. Its calculated focal length, 49.08 mm gave a power in water of 27.1±0.7 diopters. The power in water of the average human lens is 21.8 diopters, and to have obtained this power in the lens refilled herein would have required filling material of RI 1.41.

What is claimed is:

1. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens having a Young's modulus less than about 10 kPa after injection into the capsular bag of the eye.

2. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye and said polysiloxanes comprising fluoroalkyl(alkyl)siloxane monomer(s).

3. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye and said polysiloxanes being terpolymers or higher polymers of three or more siloxane monomer units, with at least one siloxane monomer having a specific gravity greater than about 1.0.

4. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye and said polysiloxanes comprising arylsiloxane monomer units, with at least one siloxane monomer having a specific gravity greater than about 1.0.

5. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye and compris-ing functional polysiloxanes having vinyl groups capable of being crosslinked, at least one multifunctional silicone hydride crosslinking agent, and an effective amount of a platinum catalyst.

6. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye and compris-ing a mixture of functional polysiloxanes having functional crosslinkable groups and non-functional polysiloxanes.

7. An injectable ophthalmic composition of polysiloxanes having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye, being essentially free from non-functional polysiloxanes, and comprising polysiloxanes with functional vinyl groups and a multifunctional hydride crosslinking agent in a relative amount so as to provide an excess of vinyl groups to hydride groups.

8. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye, being essentially free from non-functional polysiloxanes, and comprising polysiloxanes with functional vinyl groups and a multifunctional hydride crosslinking agent in a relative amount so as to provide an excess of hydride groups to vinyl groups.

9. An accommodating intraocular lens having a value of Young's modulus less than about 10 kPa that sufficiently remains stable over time, wherein said lens is made by injecting a polysiloxane composition into the capsular bag of the eye, the polysiloxane composition having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye.

10. An injectable ophthalmic composition of polysiloxanes, having a specific gravity of greater than about 1.0, a refractive index suitable for restoring the refractive power of the natural crystalline lens and a viscosity suitable for injection through a standard cannula, said composition being adapted to form an accommodating intraocular lens after injection into the capsular bag of the eye.

11. A composition according to claim 1 having a refractive index in the range of 1.38 to about 1.60.

12. A composition according to claim 1 wherein said polysiloxane composition comprises polysiloxanes having at least one siloxane monomer with a specific gravity greater than about 1.0.

13. A composition according to claim 12, wherein said polysiloxanes have a siloxane monomer —$R_aR_bSiO$—, wherein $R_a$ and $R_b$ are the same or different alkyl or phenyl groups of which at least one is substituted with one or several fluorine atoms.

14. A composition according to claim 2, wherein said monomers comprise trifluoropropylmethylsiloxane monomer.

15. A composition according to claim 4, wherein said polysiloxanes comprise methyl and substituted methylsiloxanes, phenylsiloxanes and trifluoropropylsiloxanes.

16. A composition according to claim 15, wherein said polysiloxanes are terpolymers consisting essentially of (a) dimethylsiloxane, (b) methylphenylsiloxane or diphenylsiloxane and (c) trifluoropropylmethylsiloxane monomers.

17. A composition according to claim 14, wherein said polysiloxanes comprise at least about 4 mol % trifluoropropylmethylsiloxane.

18. A composition according to claim 1 having a specific gravity within the range of about 1.03 to 1.20 and a refractive index above about 1.38.

19. A composition according to claim 1 comprising functional polysiloxanes having crosslinkable groups attached, a crosslinking agent and optionally an effective amount of a catalyst.

20. A composition according to claim 5, wherein the amount vinyl to hydride groups is larger than 1:1.

21. A composition according to claim 5, wherein the amount vinyl to hydride groups is less than 1:1.

22. A composition according to claim 5, wherein said crosslinking agent is a mixture of a difunctional hydride and a hydride with a higher functionality than two.

23. A composition according to claim 5, wherein said crosslinking agent is a tetrafunctional hydride.

24. A composition according to claim 5, wherein said crosslinking agent is a difunctional crosslinking agent.

25. A composition according to claim 24, wherein the non-functional polysiloxanes have sufficiently high molecular weight, so as to prevent diffusion through the capsular bag.

26. A composition according to claim 6, wherein the amount of non-functional polysiloxanes is within the range of about 30 to 93% (wt) of the total polysiloxane amount.

27. A composition according to claim 26, wherein the amount of non-functional polysiloxanes is within the range of about 50 to 93% (wt) of the total polysiloxane amount.

28. A composition according to claim 6, wherein the amount of non-functional polysiloxanes is within the range of about 20 to 50% (wt) of the total polysiloxane amount.

29. A composition according to claim 28 comprising vinyl substituted functional polysiloxanes and a multifunctional hydride crosslinking agent wherein the amount vinyl to hydride groups is larger than 1:1.

30. A composition according to claim 28 comprising vinyl substituted functional polysiloxanes and a multifunctional hydride crosslinking agent wherein the amount vinyl to hydride groups is less than 1:1.

31. A composition according to claim 5, further comprising non-functional polysiloxanes, and wherein the amount of vinyl to hydride groups is about 1:0.8, or higher.

32. A composition according to claim 31, wherein the amount of non-functional polysiloxanes is in excess to the functional polysiloxanes.

33. A composition according to claim 32, wherein the non-functional polysiloxanes are about 20% or less of the total amount of polysiloxanes.

34. A composition according to claim 1 having a viscosity less than about 60,000 cSt at room temperature.

35. A lens according to claim 9, having a Young's modulus less than about 5 kPa.

36. A lens according to claim 9, having a refractive index in the range of 1.38 to about 1.60.

37. A lens according to claim 9, wherein the polysiloxane composition is crosslinked in the capsular bag of the eye at ambient eye temperature.

38. A lens according to claim 37, wherein a fraction of polysiloxanes in the polysiloxane composition does not participate in the crosslinking reaction.

39. A lens according to claim 38, wherein said fraction of non-crosslinked polysiloxanes have a sufficiently high molecular weight so as to substantially prevent diffusion of the polysiloxane composition through the capsular bag.

40. A composition according to claim 1, adapted to form a lens having a Young's modulus less than about 5 kPa.

* * * * *

UNITED STATES PATENT AND TRADEMARK OFFICE
CERTIFICATE OF CORRECTION

PATENT NO.    : 6,613,343 B2
DATED         : September 2, 2003
INVENTOR(S)   : Keith A. Dillingham et al.

It is certified that error appears in the above-identified patent and that said Letters Patent is hereby corrected as shown below:

Column 17,
Lines 40, 42 and 65, change "claim 1" to -- claim 10 --.

Column 18,
Lines 1, 48 and 64, change "claim 1" to -- claim 10 --.

Signed and Sealed this

Sixteenth Day of December, 2003

JAMES E. ROGAN
*Director of the United States Patent and Trademark Office*